(12) United States Patent
Teles et al.

(10) Patent No.: US 6,756,503 B2
(45) Date of Patent: Jun. 29, 2004

(54) METHOD FOR THE PRODUCTION OF PROPYLENE OXIDE

(75) Inventors: Joaquim Henrique Teles, Otterstadt (DE); Alwin Rehfinger, Mutterstadt (DE); Peter Bassler, Viernheim (DE); Anne Wenzel, Eggenstein-Leopoldshafen (DE); Norbert Rieber, Mannheim (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/312,862

(22) PCT Filed: Jul. 5, 2001

(86) PCT No.: PCT/EP01/07716

§ 371 (c)(1),
(2), (4) Date: Jan. 2, 2003

(87) PCT Pub. No.: WO02/02544

PCT Pub. Date: Jan. 10, 2002

(65) Prior Publication Data

US 2003/0144535 A1 Jul. 31, 2003

(30) Foreign Application Priority Data

Jul. 6, 2000 (DE) .......................................... 100 32 884

(51) Int. Cl.$^7$ ............................................. C07D 301/12
(52) U.S. Cl. ....................................................... 549/531
(58) Field of Search .......................................... 549/531

(56) References Cited

U.S. PATENT DOCUMENTS

| | | | |
|---|---|---|---|
| 5,006,206 A | 4/1991 | Shih et al. | 203/55 |
| 5,107,002 A | 4/1992 | Shih | |
| 5,133,839 A | 7/1992 | Shih | 203/64 |
| 5,139,622 A | 8/1992 | Marquis et al. | 203/64 |
| 5,354,430 A | 10/1994 | Culbreth, III et al. | 203/64 |
| 6,479,680 B1 | 11/2002 | Bassler et al. | |

FOREIGN PATENT DOCUMENTS

| | | |
|---|---|---|
| DE | 100 15 246 | 3/2000 |
| EP | 0 719 768 A1 * | 7/1996 |

* cited by examiner

Primary Examiner—Amelia Owens
(74) Attorney, Agent, or Firm—Oblon, Spivak, McClelland, Maier & Neustadt, P.C.

(57) ABSTRACT

A process for the preparation of propylene oxide in which (i) propene is reacted with hydrogen peroxide in the presence of methanol to give propylene oxide, giving a mixture (Gi) comprising propylene oxide, methanol, water and unreacted hydrogen peroxide, (ii) a mixture (Gii) comprising methanol, water and hydrogen peroxide is separated off from the mixture (Gi), giving a mixture (Ga) comprising propylene oxide, and (iii) water is separated off from the mixture (Gii), giving a mixture (Giii) comprising methanol and methyl formate.

11 Claims, No Drawings

METHOD FOR THE PRODUCTION OF PROPYLENE OXIDE

This application is a 371 of PCT/EP01/07716 filed Jul. 5, 2001.

The present invention relates to a process for the preparation of propylene oxide from propene and hydrogen peroxide in the presence of methanol. After the reaction of the propene with hydrogen peroxide in the process according to the invention, a mixture comprising methanol, water and unreacted hydrogen peroxide is separated off from the reaction discharge, and this mixture is subjected to a separation process which gives a further mixture comprising methanol and methyl formate.

Processes for the preparation of propylene oxide from propene are known from the prior art. In these processes, the problem generally occurs that a certain amount of hydrogen peroxide is not reacted during the reaction and arises on subsequent removal of propylene oxide from the reaction discharge.

In order to remedy this problem, it has been proposed, inter alia, to separate off hydrogen peroxide, in an intermediate separation step, from the reaction discharge from a first reaction step and to react it again with alkene in a second reaction step. Such processes are described, for example, in PCT/EP99/05740 and DE-A 100 15 246.5. Although it is possible here to achieve virtually one hundred per cent hydrogen peroxide conversion in the second reaction step, the second reaction step does mean, however, that increased complexity is necessary.

It is an object of the present invention to provide a process in which the problem of the unreacted hydrogen peroxide arising is solved inexpensively and efficiently.

We have found that this object is achieved by a process for the preparation of propylene oxide in which (i) propene is reacted with hydrogen peroxide in the presence of methanol to give propylene oxide, giving a mixture (Gi) comprising propylene oxide, methanol, water and unreacted hydrogen peroxide, (ii) a mixture (Gii) comprising methanol, water and hydrogen peroxide is separated off from the mixture (Gi), giving a mixture (Ga) comprising propylene oxide, and (iii) water is separated off from the mixture (Gii), giving a mixture (Giii) comprising methanol and methyl formate.

Methanol is particularly preferably employed as solvent. It is also possible here to employ one or more further solvents in addition to methanol. In principle, all solvents which are suitable for the respective reaction can be employed as such further solvents. Inter alia, preference is given, for example, to water, alcohols, preferably lower alcohols, further preferably alcohols having less than 6 carbon atoms, for example ethanol, propanols, butanols and pentanols, diols or polyols, preferably those having less than 6 carbon atoms, ethers, for example diethyl ether, tetrahydrofuran, dioxane, 1,2-diethoxyethane and 2-methoxyethanol, esters, for example methyl acetate or butyrolactone, amides, for example dimethylformamide, dimethylacetamide and N-methylpyrrolidone, ketones, for example acetone, nitrites, for example acetonitrile, or mixtures of two or more of the above-mentioned compounds.

In the process according to the invention, the reaction of propene with hydrogen peroxide is preferably carried out in the presence of a catalyst. Feasible catalysts for the conversion of propylene into propylene oxide are in principle all catalysts, preferably all heterogeneous catalysts, which are suitable for the respective reaction.

Preference is given to catalysts which comprise a porous oxidic material, for example a zeolite. Preference is given to catalysts in which the porous oxidic material is a titanium-, vanadium-, chromium-, niobium- or zirconium-containing zeolite.

In particular, zeolites which contain no aluminum and in which some of the Si(IV) in the silicate lattice have been replaced by titanium as Ti(IV) exist. The titanium zeolites, in particular those having a crystal structure of the MFI type, and possibilities for their preparation are described, for example, in EP-A 0 311 983 and EP-A 0 405 978.

Titanium zeolites having an MFI structure are known for the fact that they can be identified via a certain pattern in the determination of their X-ray diffraction diagrams and in addition via a skeletal vibration band in the infrared region (IR) at about 960 cm$^{-1}$ and thus differ from alkali metal titanates or crystalline or amorphous $TiO_2$ phases.

Suitable here are, in detail, titanium-, vanadium-, chromium-, niobium- and zirconium-containing zeolites having a pentasil zeolite structure, in particular the types with X-ray assignment to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WEI, WEN, YUG or ZON structure and to mixed structures consisting of two or more of the above-mentioned structures. Also feasible for use in the process according to the invention are titanium-containing zeolites having the UTD-1, CIT-1 or CIT-5 structure. Further titanium-containing zeolites which may be mentioned are those having the ZSM-48 or ZSM-12 structure.

Ti zeolites having the MFI, MEL or MFI/MEL mixed structure are regarded as particularly preferred for the process according to the invention. Preference is furthermore given, in detail, to the Ti-containing zeolite catalysts generally known as "TS-1", "TS-2" and "TS-3", and Ti zeolites having a skeletal structure which is isomorphous with beta-zeolites.

In the process according to the invention, particular preference is given to a heterogeneous catalyst comprising the titanium-containing silicalite TS-1.

Accordingly, the present invention also relates to a process as described above in which, for the preparation of the propylene oxide, a zeolite catalyst, preferably a titanium silicalite catalyst and in particular a titanium silicalite catalyst of the structure TS-1, is employed.

The removal of water from the mixture (Gii) is in the process according to the invention preferably carried out by distillation, it being possible to use one or alternatively a plurality of distillation columns. Use of one or two distillation columns is preferred. In the case that heat recovery is unnecessary, one distillation column is preferably used. Two or more distillation columns are preferably used if particularly good heat integration in the process is to be ensured.

Regarding the physical parameters, such as temperature or pressure, there are no particular restrictions during removal of water from the mixture (Gii) by distillation, so long as it is ensured that hydrogen peroxide is degraded during the distillation and a mixture (Giii) comprising methyl formate and methanol is obtained.

If only one column is employed for the removal of water from the mixture (Gii) in the process according to the invention, this preferably has at least 5, preferably at least 20 and further preferably at least 30 theoretical plates. The distillation is preferably carried out at pressures in the range from 0.5 to 40 bar, preferably from 1.0 to 20 bar and particularly preferably from 2 to 15 bar.

If two columns are employed for the removal of water from the mixture (Gii) in the process according to the invention, the pressures are then selected in such a way that the heat of condensation at the top of the columns can be used to heat other process streams. This is achieved, for example, by cooling the condenser of at least one column using, for example, water and employing the hot water resulting from the cooling or the steam resulting from the cooling to heat one or more steps of the process according to the invention or even one or more other processes.

The first distillation column is preferably operated at pressures in the range from 0.5 to 40 bar and preferably from 1 to 20 bar. In a possible embodiment, the first column is operated at a higher pressure level than the second column. In this case, the bottom of the second column is heated using the vapors from the first column. In a preferred embodiment, the first column is operated at a lower pressure level than the second column. In this case, the bottom of the first column is heated using, the vapors from the second column.

In a particularly preferred embodiment, the first column is operated at pressures in the range from 4 to 9 bar and further preferably in the range from 6 to 8 bar and the second column is operated at pressures in the range from 11 to 16 bar and further preferably in the range from 12 to 14 bar. In general, from 20 to 80%, preferably from 30 to 70% and particularly preferably from 40 to 60% of the methanol present in the mixture (Gii) is separated off at the top of the first column together with methyl formate. The mixture obtained at the bottom of the first column is used as feed for the second column. The top product from the second column comprises the residual methanol and methyl formate, and the bottom product comprises water. The top product from the first columns and the top product from the second column are combined to give the mixture (Giii).

Both in the case of removal of water in two columns and in the case of removal of water in one column, the separation conditions are particularly preferably selected so that the water content in the mixture (Giii) is generally less than 3% by weight, preferably less than 1% by weight and particularly preferably less than 0.3% by weight. The separation conditions are further preferably selected so that the methanol content in the bottom take-off is less than 5% by weight, preferably less than 1% by weight and particularly preferably less than 0.2% by weight.

As further components, the bottom take-off may in addition comprise, inter alia, methoxypropanols, propylene glycol, formic acid, dipropylene glycol monomethyl ether and formaldehyde, for example.

Accordingly, the present invention also relates to a process as described above in which the water is separated off by distillation in (iii), wherein (w) a mixture (Gw) which principally comprises methanol and methyl formate is separated off from the mixture (Gii) at the top of a first distillation column, (x) the mixture obtained at the bottom of the first distillation column is fed as feed to a second distillation column, (y) a mixture (Gy) which principally comprises methanol and methyl formate is obtained at the top of the second distillation column, and (z) the mixtures (Gw) and (Gy) are combined to give the mixture (Giii).

The mixture (Giii) obtained after the removal of water is, in a preferred embodiment of the process according to the invention, fed to a further work-up step, in which methanol is separated from methyl formate in the mixture (Giii).

In a further preferred embodiment of the process according to the invention, the methanol obtained in this way is recycled into (i).

The present invention therefore also relates to a process as described above in which methanol is separated from methyl formate in the mixture (Giii), and the methanol separated off is recycled into (i).

The removal of the methanol from the mixture (Giii) comprising methyl formate and methanol can in principle be achieved here by all conceivable methods, so long as it is ensured that the purity of the separated off methanol satisfies the demands set.

Mention may be made here, inter alia, of chemical methods. For example, it is possible to bring the mixture comprising methanol and methyl formate into contact with a suitable basic ion exchanger, producing methanol, while the formate remains on the ion exchanger. This process is described, inter alia, in U.S. Pat. No. 5,107,002.

Furthermore, the mixture comprising methanol and methyl formate can be treated with a base, with the methyl formate being hydrolyzed. All bases by means of which the hydrolysis of the methyl formate can be achieved can be used here. Preference is given to strong bases. Particularly preferred bases for the purposes of the present invention are salts of acids which are weaker acids than formic acid. Inter alia, preference is given here to, for example, alkali metal and alkaline earth metal hydroxides and alkali metal salts of alcohols or phenols. It is of course also possible to use mixtures of two or more of these bases.

The removal of methanol from the mixture comprising methanol and methyl formate can furthermore preferably be carried out using physical methods, for example distillation methods.

Of these, extractive distillation methods, for example, as known from the prior art and described, for example, in the above-mentioned U.S. Pat. No. 5,107,002, are possible.

However, preference is given to distillation methods, which require less complex equipment than said extraction distillation methods.

Preference is given to a distillation method in which one or more columns, further preferably one column, is employed. If one column is employed, this has at least five, preferably at least 10 and in particular at least 20 theoretical plates.

The pressures preferably used are generally in the range from 0.2 to 50 bar, preferably in the range from 1.5 to 30 bar and in particular in the range from 2.0 to 20 bar.

The head temperatures and bottom temperatures are clearly determined by the selected pressure. In a particularly preferred embodiment, this column, which has approximately 20 theoretical plates, is operated at pressures in the range from 2.0 to 20 bar. The top product obtained is a mixture comprising methyl formate and a small proportion of the methanol present in the feed. This mixture preferably has a methanol content of less than 80% by weight, preferably less than 50% by weight and particularly preferably less than 20% by weight.

It is furthermore conceivable for the mixture (Giii) comprising methanol and methyl formate to contain additional further components besides methyl formate. The term "components" here denotes both pure compounds and also azeotropes which have a boiling point which is lower than the boiling point of methanol. As such components, mention may be made, inter alia, by way of example of acetaldehyde, 1,1-dimethoxyethane, propionaldehyde, 1,1-dimethoxypropane, acetone or 2,4 dimethyl-1,3-dioxolane. These can likewise be separated off from the mixture during the work-up.

It is thus possible to separate off these by-products from the mixture by one or more suitable physical or chemical methods before separation of the methanol from methyl formate. It is likewise possible firstly to separate off methanol from the mixture, which can give a mixture comprising methanol and at least one impurity. In this case, the removal of methanol from the mixture can be followed by one or more separation steps in which methanol is separated from the at least one impurity. The removal of methanol from the mixture can likewise result in a mixture comprising methyl formate and one or more impurities. This too can, if necessary, be separated into its constituents by one or more suitable physical or chemical methods. The constituents can then be separated or fed together as starting materials to one or more further processes or sent to heat recovery.

Depending on the chemical nature of the impurities, it is also possible to separate off methanol from the mixture by separating both methyl formate and the at least one impurity from methanol in a single process step.

The distillation preferably employed in accordance with the invention and described as above gives a methanol fraction which has a content of methyl formate of in general less than 500 ppm, preferably less than 100 ppm and in particular preferably less than 20 ppm.

Depending on the demands made of the purity of the methanol fraction, residues of other components, for example acetaldehyde, 1,1-dimethoxyethane, propionaldehyde, 1,1-dimethoxypropane, acetone or 2,4-dimethyl-1,3-dioxolane, remaining in the methanol fraction after the distillative work-up can be separated from the methanol by one or more suitable measures, for example one or more further distillations.

In general, it is entirely sufficient if the concentration of each individual secondary component in the methanol is less than 1% by weight and the sum of all secondary components does not exceed 5% by weight.

The methanol separated off from the methyl formate in this way can be re-used, it being in principle conceivable to recycle the methanol into the process for the preparation of propylene oxide or, if necessary, to feed it to a different process in which methanol is required as solvent or as starting material or in another function. It is of course conceivable to divide the methanol stream resulting from the separation according to the invention into two or more streams and to feed each stream to a different process.

In a particularly preferred embodiment of the process according to the invention, the methanol separated from methyl formate and, if necessary, from one or more secondary components or impurities is recycled, as described above, into the process for the preparation of propylene oxide. The methanol is preferably, inter alia, pumped into a buffer tank and fed into the process therefrom.

As far as the preparation of propylene oxide in (i) is concerned, this is very particularly preferably carried out in one step. The term "one step" as used for the purposes of the present application denotes process procedures in which no removal of hydrogen peroxide takes place. For the purposes of the present invention, a one-step process thus covers, inter alia, processes in which the starting materials are reacted with one another in a reactor, and the reaction discharge is processed further, and also, inter alia, processes in which propene is reacted with hydrogen peroxide in a first reaction step to give a product stream, the product stream is fed to at least one intermediate treatment, with a further product stream being obtained from the intermediate treatment, and the further product stream is fed to a further reaction step, in which hydrogen peroxide is reacted with propene, where the intermediate treatments are not removals of hydrogen peroxide.

Further reaction steps are of course also conceivable, where an intermediate treatment can, but need not, take place between two reaction steps. A conceivable intermediate treatment is, inter alia, for example the addition of a base to a product stream, it particularly preferably being possible to employ basic compounds which influence the reaction of hydrogen peroxide with propene in the desired manner in the process according to the invention. If, for example, zeolites are employed as heterogeneous catalysts, preference is given to basic compounds which lower the acidity of these zeolites. Such bases are described, for example, in DE-A 100 15 246.5, which is incorporated into the present application in its full scope in this respect by way of reference.

Concerning, for example, the arrangement and type of the reactors employed in (i), all suitable reactors are also conceivable here. In particular, use can be made, for example in one or more of the above-mentioned reaction steps, of two or more reactors connected in parallel. In this respect, reference is made to DE-A 100 15 246.5, which is incorporated into the present application in its full scope with respect to the possible reactor arrangements by way of reference.

The present invention therefore relates to a process as described above in which the reaction in (i) is carried out in one step.

Furthermore, the temperature and pressure of the reaction medium can be changed during the process in the course of the preparation of propylene oxide from propene and hydrogen peroxide. The pH and temperature of the reaction medium can likewise be changed. It is furthermore possible additionally to change the pressure under which the reaction takes place in addition to the pH and temperature of the reaction medium. In this respect, reference is made to DE-A 199 36 547.4, which is incorporated into the present application in its full scope in this respect by way of reference.

The preparation of propylene oxide in (i) is particularly preferably carried out in such a way that the conversion of hydrogen peroxide is generally in the range from 85 to 99.99%, preferably in the range from 90 to 99.9% and particularly preferably in the range from 95 to 99.5%.

The present invention therefore also relates to a process as described above in which the hydrogen peroxide conversion in (i) is in the range from 85 to 99.99%.

In accordance with the invention, a mixture (Gii) comprising methanol, water and hydrogen peroxide is separated off from the mixture (Gi), giving a mixture (Ga) comprising propylene oxide. This separation can generally be carried out by any suitable method. The separation is preferably carried out by distillation.

Preference is given to a distillation method in which one or more columns are employed, further preferably one column is employed. If one column is employed, this has at least 5, preferably at least 10 and in particular at least 15 theoretical plates. The pressures preferably used are generally in the range from 0.5 to 10 bar, preferably in the range from 0.8 to 3 bar and in particular in the region of the ambient pressure.

The top and bottom temperatures are clearly determined by the selected pressure. In a very particularly preferred embodiment, this column, which has about 15 theoretical plates, is operated at ambient pressure. The top product obtained at a head temperature in the region of approximately 35° C. is a mixture (Ga) comprising propylene oxide. The bottom product obtained at a bottom temperature of approximately 68° C. is a mixture (Gii) comprising methanol, water and unreacted hydrogen peroxide.

The mixture (Gii) may, in addition to methanol, water and hydrogen peroxide, comprise one or more further compounds which can be, for example, by-products of the reaction in (i) or compounds formed during the separation in (ii), or compounds introduced into (i) as impurities in the starting materials, or solvents employed, for example, in addition to the solvent methanol, or compounds employed for the distillative separation in (ii), or compounds added, for example, during an intermediate treatment as described above. In the preparation of propylene oxide from propene in (i), the mixture (Gii) may comprise, inter alia, 1,1 dimethoxyethane, acetone, acetaldehyde, 1,1-dimethoxypropane, propionaldehyde, methyl formate and/or 2,4 dimethyl-1,3-dioxolane.

In addition to propylene oxide, the mixture (Ga) may likewise comprise one or more further compounds, which can again be, for example, by-products of the reaction in (i) or compounds formed in the separation in (ii), or compounds introduced into (i) as impurities in the starting materials, or methanol or solvents employed, for example, in addition to the solvent methanol, or compounds employed for the distillative separation in (ii), or compounds added, for example, during an intermediate treatment as described above.

Depending on the process procedure, it is conceivable in the process according to the invention for the mixture (Ga) obtained from the reaction discharge in (i) to comprise methanol in addition to propylene oxide. Preferred methanol contents are in the range from 10 to 90% by weight, particularly preferably in the range from 25 to 75% by weight and very particularly preferably in the range from 40 to 60% by weight of methanol.

In a further preferred embodiment, inter alia, the methanol present in (Ga) is separated off from (Ga) and added to the mixture (Gii). For the purposes of the present application, the expression "added to the mixture (Gii)" covers both embodiments of the process according to the invention in which the methanol separated off from (Ga) is firstly added to (Gii), and the resultant mixture is fed to process step (iii), and embodiments in which the methanol separated off from (Ga) and the mixture (Gii) are fed separately to process step (iii), and not until there do they come into contact.

The methanol may furthermore also be added to the mixture (Giii).

The present invention therefore also relates to a process as described above where the mixture (Ga) comprises methanol in addition to propylene oxide, wherein methanol is separated off from (Ga) and added to the mixture (Gii) or the mixture (Giii) or the mixtures (Gii) and (Giii).

The removal of the methanol from the mixture (Ga) comprising methanol and propylene oxide is preferably carried out by a distillative method, with the number of columns employed being essentially as desired. Preference is given to the use of one column. This column preferably has at least 20, preferably at least 40 and further preferably at least 60 theoretical plates.

The distillation in this column is preferably carried out at pressures in the range from 0.3 to 10 bar, preferably from 0.4 to 2 bar and particularly preferably from 0.6 to 1.2 bar.

The present invention therefore also relates to a process in which methanol is separated off from (Ga) and is as described above, wherein the removal of the methanol is carried out in a column having at least 20 theoretical plates at pressures in the range from 0.3 to 10 bar.

The reaction discharge from (i) may comprise propene which has not reacted in (i). This is preferably separated off from the reaction discharge.

In a preferred embodiment of the process according to the invention, the removal of the unreacted propene is carried out during the removal of the mixture (Gii) in process step (ii). In a further preferred embodiment, the distillative separation in (ii) is carried out by, for example, separating off the mixture (Gii) at the bottom, separating off the mixture (Ga) via a side take-off of the distillation column, and separating off the unreacted propene at the top.

In a likewise preferred embodiment of the process according to the invention, the separation in (ii) is carried out in such a way that the mixture (Ga) obtained from (ii) comprises propene which has not reacted in (i) in addition to propylene oxide and possibly methanol. This propene is preferably separated off from (Ga) during the further process.

The present invention therefore also relates to a process as described above where the mixture (Ga), in addition to propylene oxide and possibly methanol, additionally comprises propene which has not reacted in (i), wherein the propene is separated off from the mixture (Ga).

The removal of the unreacted propene from (Ga) is preferably carried out by distillation. The number of columns employed is essentially as desired. Preference is given to the use of one column. This column generally has at least 5, preferably at least 10 and further preferably at least 15 theoretical plates. The distillation in this column is preferably carried out at pressures in the range from 0.5 to 25 bar, preferably from 0.7 to 5 bar and particularly preferably in the range from 0.9 to 1.5 bar.

During the removal of the unreacted propene, the problem may under certain circumstances occur that during removal of the propene as low-boiling fraction, as described above, oxygen may accumulate in this low-boiling fraction in a concentration which turns the low-boiling fraction into an ignitable mixture. This can cause a serious safety risk if propene is in turn separated off from the low-boiling fraction by distillation, which is preferably the case if the propene is to be recycled into (i).

This problem can be solved, for example, by removing the propene from the low-boiler mixture by distillation and introducing an inert substance having a boiling point which is lower than that of propene, preferably methane, into the upper part of the separation device used for this purpose in such an amount that the oxygen is diluted to a concentration at which the mixture is no longer ignitable. This process is described, for example, in EP-B 0 719 768. However, the problem is preferably solved by using a process for the work-up of a mixture comprising propene and oxygen in which oxygen is separated off from the mixture by non-distillative methods to give a further mixture, and the propene is separated off from the further mixture by distillation. This process is described in DE-A 100 01 401.1, which is incorporated into the present application in its full scope in this respect by way of reference.

In a particularly preferred embodiment of the process according to the invention, the propene separated off is recycled into (i) as starting material.

In a further particularly preferred embodiment, all said process steps are carried out continuously. It is of course also possible to operate one or more of the steps in a batch procedure.

We claim:

1. A process for the preparation of propylene oxide in which
   (i) propene is reacted with hydrogen peroxide in the presence of methanol to give propylene oxide, giving a mixture (Gi) comprising propylene oxide, methanol, water and unreacted hydrogen peroxide,
   (ii) a mixture (Gii) comprising methanol, water and hydrogen peroxide is separated off from the mixture (Gi), giving a mixture (Ga) comprising propylene oxide, and
   (iii) water is separated off from the mixture (Gii), giving a mixture (Giii) comprising methanol and methyl formate.

2. A process as claimed in claim 1, wherein the propylene oxide is prepared using a zeolite catalyst.

3. A process as claimed in claim 1, in which the water is separated off by distillation in (iii), wherein
   (w) a mixture (Gw) which principally comprises methanol and methyl formate is separated off from the mixture (Gii) at the top of a first distillation column,
   (x) the mixture obtained at the bottom of the first distillation column is fed as feed to a second distillation column,
   (y) a mixture (Gy) which principally comprises methanol and methyl formate is obtained at the top of the second distillation column, and
   (z) the mixtures (Gw) and (Gy) are combined to give the mixture (Giii).

4. A process as claimed in claim 1, wherein methanol is separated from methyl formate in the mixture (Giii), and the methanol separated off is recycled into (i).

5. A process as claimed in claim 1, wherein the reaction in (i) is carried out in one step.

6. A process as claimed in claim 5, wherein the hydrogen peroxide conversion in (i) is in the range from 85 to 99.99%.

7. A process as claimed in claim 1, where the mixture (Ga) comprises methanol in addition to propylene oxide, wherein methanol is separated off from (Ga) and added to the mixture (Gii) or the mixture (Giii) or the mixtures (Gii) and (Giii).

8. A process as claimed in claim 7, wherein the removal of the methanol is carried out in a column having at least 20 theoretical plates at pressures in the range from 0.3 to 10 bar.

9. A process as claimed in claim 1, where the mixture (Ga), in addition to propylene oxide and possibly methanol, additionally comprises propene which has not reacted in (i), wherein the propene is separated off from the mixture (Ga).

10. The process as claimed in claim 1, wherein the propylene oxide is prepared using a silicalite catalyst.

11. The process as claimed in claim 1, wherein the propylene oxide is prepared using a titanium silicalite catalyst having the TS-1 structure.

* * * * *